United States Patent
Hoffman et al.

(10) Patent No.: US 9,782,118 B2
(45) Date of Patent: Oct. 10, 2017

(54) DIAGNOSIS OF SWALLOWING DISORDERS USING HIGH RESOLUTION MANOMETRY

(71) Applicant: Wisconsin Alumni Research Foundation, Madison, WI (US)

(72) Inventors: Matthew Richard Hoffman, Madison, WI (US); Jack J Jiang, Wilmette, IL (US); Zhixian Geng, Madison, WI (US); Timothy Michael McCulloch, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 880 days.

(21) Appl. No.: 13/896,831

(22) Filed: May 17, 2013

(65) Prior Publication Data

US 2014/0343415 A1  Nov. 20, 2014

(51) Int. Cl.
*A61B 5/00* (2006.01)
*A61B 5/03* (2006.01)
*A61B 6/00* (2006.01)

(52) U.S. Cl.
CPC ............ *A61B 5/4205* (2013.01); *A61B 5/037* (2013.01); *A61B 5/4233* (2013.01); *A61B 6/481* (2013.01); *A61B 6/485* (2013.01); *A61B 5/7282* (2013.01); *A61B 6/487* (2013.01); *A61B 6/5217* (2013.01); *A61B 2562/0247* (2013.01)

(58) Field of Classification Search
CPC ..... A61B 5/4205; A61B 5/037; A61B 5/7282; A61B 6/481; A61B 1/2733; A61B 6/485
USPC .................................................. 600/561, 593
See application file for complete search history.

(56) References Cited

U.S. PATENT DOCUMENTS

| | | | |
|---|---|---|---|
| 2009/0003669 A1* | 1/2009 | Parks ..................... | A61B 5/037 382/128 |
| 2009/0222065 A1* | 9/2009 | Dlugos, Jr. .............. | A61B 5/03 607/60 |
| 2013/0296662 A1* | 11/2013 | Omari .................... | A61B 5/037 600/301 |

OTHER PUBLICATIONS

Jason D. Mielens, Matthew R. Hoffman, Michelle R. Ciucci, Jack J. Jiang, Timothy M. McCulloch; Automated Analysis of Pharyngeal Pressure Data Obtained with High-Resolution Manometry; Springer Science + Business Media, LLC, 2010; pp. 3-12; Dysphagia (2011); Madison, WI; US.
Jason D. Mielens, Matthew R. Hoffman, Michelle R. Ciucci, Timothy M. McCulloch, Jack J. Jiang; Application of Classification Models to Pharyngeal High-Resolution Manometry; JSLHR Article; Journel of Speech, Language and Hearing Research; Jun. 2012; pp. 892-902; vol. 55; American Speech-Language-Hearing Association; Madison, WI; US.
Matthew R. Hoffman, Jason D. Mielens, Taher I. Omari, Nathalie Rommel, Jack J. Jiang, Timothy M. McCulloch; Artificial Neural Network Classification of Pharyngeal High-Resolution Manometry With Impedance Data; Research Paper; 2012; pp. 1-8; Laryngoscope 000: Month 2012; US.

(Continued)

*Primary Examiner* — Max Hindenburg
*Assistant Examiner* — Jonathan M Foreman (57) ABSTRACT

Parameters extracted from high definition manometric measurements of the pharynx and upper esophagus at preidentified locations and times are applied to a supervised learning machine trained using x-ray fluoroscopy data to provide diagnostic information comparable to that of x-ray fluoroscopy without radiation exposure.

22 Claims, 3 Drawing Sheets

(56) References Cited

OTHER PUBLICATIONS

Zhixian Geng. Matthew R. Hoffman, Corrinne A. Jones, Timothy M. McCulloch, Jack J. Jiang; Three-Dimensional Analysis of Pharyngeal High-Resolution Manometry Data; Article; 2013; pp. 1-8; Laryngoscope 00: Month 2013; US.

Matthew R. Hoffman, Corrine A. Jones, Zhixian Geng, Suzann M. Abelhalim, Chelsea C. Walczak, Alyssa R. Mitchell, Jack J. Jiang, Timothy M. McCulloch; Classification of High-Resolution Manometry Data According to Videofluoroscopic Parameters Using Pattern Recognition; Research Paper; 2013; Article No. 489506; pp. 1-8; Otolaryngology-Head and Neck Surgery XX(X); US.

* cited by examiner

DIAGNOSIS OF SWALLOWING DISORDERS USING HIGH RESOLUTION MANOMETRY

STATEMENT REGARDING FEDERALLY SPONSORED RESEARCH OR DEVELOPMENT

This invention was made with government support under DC011130 awarded by the National Institutes of Health. The government has certain rights in the invention.

CROSS REFERENCE TO RELATED APPLICATION

BACKGROUND OF THE INVENTION

The present invention relates to an apparatus and method for diagnosing swallowing disorders (dysphagia) using high resolution manometry and in particular to a computerized method providing automatic or semiautomatic analysis of complex high resolution manometry data.

Eating and drinking, the primary means by which we meet nutritional requirements, necessitates the ability to swallow. Approximately 15 million Americans suffer from swallowing disorders. Individuals of any age can be affected and disorders are particularly likely in persons with any neurological disorder, acid reflux, and cancer of the head and neck. Dysphagia affects the aging population and the leading cause of death in Parkinson's disease is aspiration pneumonia, a result of being unable to protect the airway during swallowing.

Videofluoroscopy is a primary examination tool providing information on swallowing disorders and can provide information on bolus transit, residue, and aspiration used to guide assessment and therapy. The Modified Barium Swallow Impairment Profile (MBSImP), when used with videofluoroscopy, provides a method of standardized videofluoroscopic assessment that provides measures of 17 diagnostic components characterizing the oral, pharyngeal, and esophageal phases of swallowing. By viewing x-ray images, highlighted with a barium contrast agent, trained individuals can extract the MBSImP components to accurately describe the movement and timing of various structures associated with swallowing and to diagnose swallowing disorders.

While videofluoroscopy is a valuable tool for assessing swallowing disorders, videofluoroscopic examination requires radiation exposure and its associated risk to patients. Additionally, such x-ray examinations normally require that the patient be moved to the radiology suite, which may be difficult or impractical for some patients, and are a relatively poor predictor of aspiration pneumonia.

Thus, it would be beneficial to develop an assessment of swallowing that can provide information similar to that provided by videofluoroscopy but does not require radiation exposure and that can also be performed easily at the bedside. Such an assessment would also be amenable to serial measurements and evaluation of patient progress over time, as the exam could be performed quickly and accumulative radiation would not be a concern.

SUMMARY OF THE INVENTION

The present invention provides a method of assessing swallowing disorders using data from high resolution manometry, in which a manometric catheter is inserted along the pharynx and esophagus to provide substantially continuous pressure readings at regularly spaced intervals along the pharynx and esophagus during the swallowing process. Despite the lack of an actual image of the type provided by videofluoroscopy, the inventors have determined that sufficient data can be extracted from these pressure readings to provide salient therapeutic information alone and act as an accurate proxy for measurements of the type made by videofluoroscopy. For this reason, it is believed that such manometric data can provide a substitute for videofluoroscopy and, further, may provide sufficient information for independent diagnosis of swallowing disorders.

Specifically then, in one embodiment the invention provides a system for diagnosing swallowing disorders using a manometer adapted to be inserted along the upper aerodigestive tract in the vicinity of the pharynx and esophagus to provide a series of pressure measurements at different points along the upper pharynx and superior esophagus. A computer receives the series of pressure measurements at different points and executes a stored program to identify the changes in pressure measurements during a swallowing along multiple predetermined locations within the pharynx and superior esophagus and to analyze pressure as a function of time in the predetermined locations to generate a set of predetermined parameters. The parameters are then mapped to diagnostic values indicating swallowing function and the diagnostic values are output to a user.

It is thus a feature of at least one embodiment of the invention to provide reliable and reproducible diagnosis of swallowing disorders by analyzing pressure changes at different points in the pharynx and superior esophagus without the need for x-ray exposure and while using equipment suitable for bedside or office based use. It is another feature of at least one embodiment of the invention to provide a direct measure of the forces impacting bolus movement and to provide a system that can provide information about swallow function with direct therapeutic agents.

The linking of pressures to predetermined locations may identify the predetermined locations using time-varying pressure patterns having the dimensions of distance along the pharynx and superior esophagus and time.

It is thus a feature of at least one embodiment of the invention to provide diagnosis of swallowing disorders without the need for a conventional two-dimensional image of swallowing structure such as provided by an x-ray fluoroscopy image.

The identification of pressures to predetermined locations may receive input from a user viewing the pressure pattern to identify at least one point associated with a predetermined location.

It is thus a feature of at least one embodiment of the invention to take advantage of the intrinsic pattern recognition abilities of the user in registering the pressure pattern with the anatomy of the patient.

The program may combine location data received from the user with other data from the pressure pattern to identify the predetermined locations.

It is thus a feature of at least one embodiment of the invention to allow the input from the user to be treated as "seed data" only, that are then refined by the program using the information from the pressure pattern to provide a repeatable and accurate location.

The manometer may provide for pressure measurements with no greater than 1 cm separation along the pharynx.

It is thus a feature of at least one embodiment of the invention to manage the large amount of complex pressure data obtainable in high resolution manometry.

The predetermined locations may include the velopharynx, and the upper esophageal sphincter. Further the program may include the step of identifying a time of opening of the upper esophageal sphincter. In some embodiments, the predetermined parameters for the predetermined regions may include maximum pressure, rise time, rise rate, fall-time, and duration of pressure above the baseline, duration between opening and closure peak pressures and nadir pressures and nadir pressure duration. In some embodiments, the maximum pressures may include peak pressure before opening of the upper esophageal sphincter and a peak pressure after opening of the upper esophageal sphincter. In some embodiments the predetermined locations include the mesopharynx and the upper edge of the esophageal sphincter.

It is thus a feature of at least one embodiment of the invention to extract a set of parameters from the large amount of data represented by a high resolution manometry pressure pattern that may be reliably mapped to swallowing disorder diagnoses.

The diagnostic values may conform to those provided by a videofluoroscopic exam, for example, one analyzed using the modified barium swallow impairment profile (MBSImP) assessment. These diagnostic values may include initiation of pharyngeal swallow, laryngeal elevation, anterior hyoid excursion, epiglottic movement, pharyngeal stripping wave, pharyngoesophageal segment closing, tongue base retraction, penetration and or/ aspiration, and pharyngeal residue, and could also include pharyngeal constriction ratio (pharyngeal area at maximum contraction by the pharyngeal area at rest)

It is thus a feature of at least one embodiment of the invention to provide a familiar set of parameters to clinicians normally obtained with x-rays, without the x-ray exposure.

Alternatively or in addition, the diagnosis may provide an indication of normal or abnormal swallowing function.

It is thus a feature of at least one embodiment of the invention to process the complex data of high resolution manometry to produce a simple diagnostic output indicating abnormality or not.

Alternatively or in addition, the diagnosis may provide an indication of a cause of the swallowing disorder selected from the group consisting of: cricopharyngeus abnormality, glottic insufficiency, pharyngeal stiffness/fibrosis, neurological disorder, Zenker's diverticulum, head and neck cancer, recurrent hiatal hernia, idiopathic muscular atrophy, Schatzki's ring, generalized weakness, and discoordination.

It is thus a feature of at least one embodiment of the invention to aid the clinician in identifying specific originations of swallowing disorders.

The diagnostic value may include a confidence value indicating a confidence in the diagnosis.

It is thus a feature of at least one embodiment of the invention to provide confidence values indicating likelihood of correct diagnosis in the face of inherent uncertainties in diagnosis.

In addition, the system may provide a recommended therapy.

It is thus a feature of at least one embodiment of the invention to provide a convenient reference to the clinician recommending therapies and therapeutic targets for the specifically identified diagnosis and specific abnormalities of a patient's swallow.

The mapping performed by the program may use supervised machine learning based on a training set of clinically acquired swallow measurements each linked to a diagnostic value.

It is thus a feature of at least one embodiment of the invention to provide a mechanism for mapping complex data to diagnostic information that may not be amenable to human-derived rules.

The linking to diagnostic values of the training set may employ contemporary measurements with the manometer and videofluoroscopic assessments such as the modified barium swallow impairment profile (MBSImP).

It is thus a feature of at least one embodiment of the invention to inform the assessment process of the present invention with insights derivable from x-ray fluoroscopy.

It is also a feature of at least one embodiment of the invention to inform the assessment process of the present invention with insights from functional endoscopic evaluation of swallowing (FEES).

These particular objects and advantages may apply to only some embodiments falling within the claims and thus do not define the scope of the invention.

DETAILED DESCRIPTION OF THE PREFERRED EMBODIMENT

Figure 1:
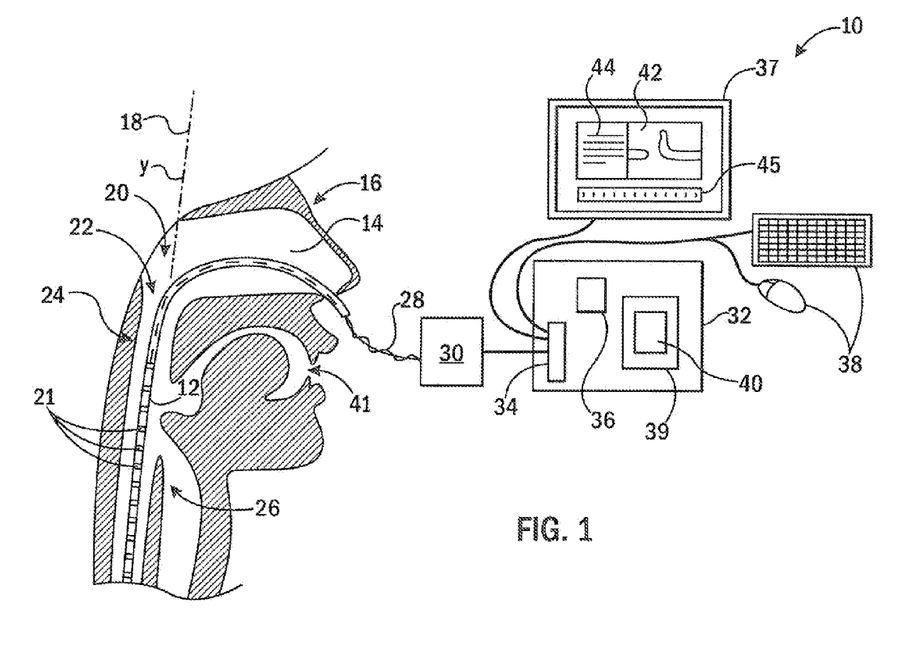
FIG. 1 is a block diagram of a high resolution manometry system suitable for use with the present invention providing a computer for analyzing received pressure data taken at points along the pharynx during a swallow and displaying diagnosis information.

Referring now to FIG. 1, a high resolution manometry system 10 for use with the present invention may provide a high resolution manometric catheter 12 inserted through the nasal passages 14 of a patient 16 to lie along a y-axis 18 extending generally along patient's pharynx 20. The sensing portion of the catheter 12 provides for multiple omnidirectional pressure sensors 21 positioned approximately 1 every centimeter along a length of the sensing portion of the catheter 12 to lie near the velopharynx 22 and extend down through the mesopharynx 24 and through the upper esophageal sphincter 26.

The catheter 12 may communicate via electrical lead 28 with a signal decoder 30 providing a set of separate, substantially continuous pressure readings from each of the pressure sensors 21. In one example, the catheter 12 and signal decoder 30 may be a ManoScan High Resolution Manometry System such as is commercially available from Sierra Scientific Instruments of Los Angeles, Calif. This example catheter 12 has an outer diameter of approximately 4 millimeters and 36 circumferential pressure sensors 21 each recording pressures between −20 millimeters of mercury and 600 millimeters of mercury with an accuracy of two millimeters of mercury and a data acquisition rate of 50 hertz.

Referring still to FIG. 1, output from the signal decoder 30 may be provided to an electronic computer 32 via an interface 34. The interface 34 may also provide communication to the graphics display 37 and user input device 38 such as a keyboard mouse or the like. The computer 32 includes at least one processor 36 communicating with the interface 34 and with a solid-state or other non-transient memory 39 holding a program 40 as will be described in more detail below.

Generally, the computer 32 may receive pressure information from the catheter 12 to present on the display a three-dimensional pressure pattern 42 having one dimension (a horizontal axis) of time and a second dimension (a vertical axis) of distance along the pharynx y-axis 18 and a third dimension (a mapping to grayscale or color) of pressure. As used herein, the pressure pattern 42 will refer not only to the image, but also the underlying data structure as context demands. In the present invention, the pressure pattern 42 will be processed by the processor 36 according to the stored program 40 to provide for diagnostic outputs 45 that may also be displayed to the user. The user input device 38 will be used as part of this process as will also be described.

Figure 2:
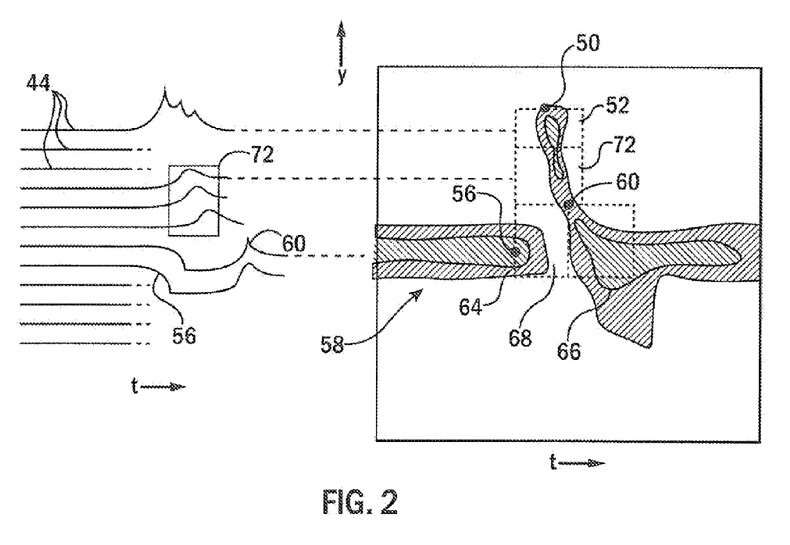
FIG. 2 is a set of time-aligned pressure profiles taken at different locations along the pharynx adjacent to a three-dimensional pressure map in which pressure amplitude is expressed as shading or color.

Referring now to FIG. 2, the pressure pattern 42 may be derived from a series of pressure profiles 44 representing a time sequence of the signals from each of the sensors 21 of the catheter 12, each providing for one row of data in the pressure pattern 42.

Figure 3:
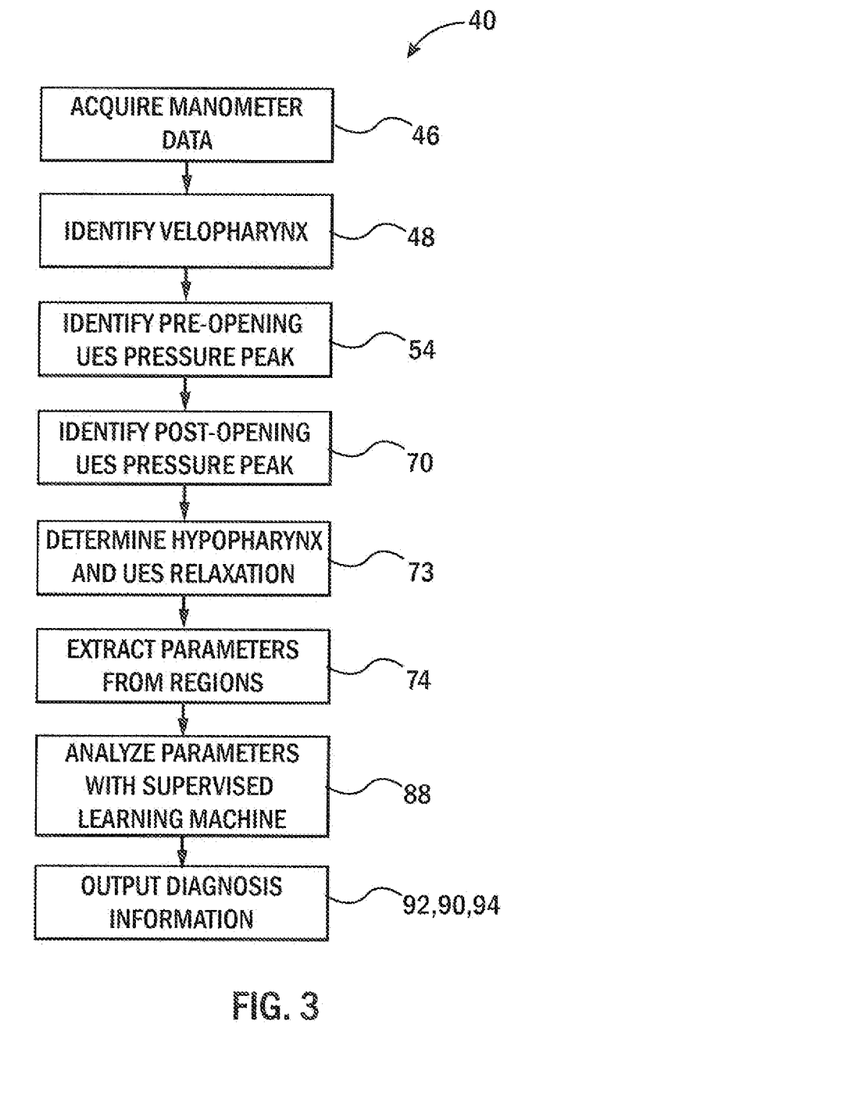
FIG. 3 is a flowchart of a program executed by the computer of FIG. 1 providing the displayed diagnosis and treatment planning information of FIG. 1 using supervised machine learning.

Referring now to FIGS. 2 and 3, the program 40 may begin as indicated by process block 46 by calibration of the catheter 12 according to the manufacturer's instructions and acquiring a set of pressure profiles 44 comprising manometric data from the catheter 12 while the patient swallows a predetermined standard bolus. The bolus size may, for example, range from one cubic centimeter to 20 cubic centimeters and maybe a liquid (water or saline) introduced through the oral cavity via syringe, or a semisolid (pudding) introduced through the oral cavity 41 via spoon.

At succeeding process block 48, pressure data of the pressure profiles 44 may be displayed in a pressure pattern 42 to the user on the display 37 together with the series of pressure profiles 44 aligned therewith as shown in FIG. 2. At this time, the user is instructed to identify the general region of the velopharynx 22 from the displayed pressure pattern 42. In one embodiment, the user may manipulate a cursor to locate it at a cursor position 50 to the top of the velopharynx. The program 40 then automatically identifies a velopharynx region 52 proximate to the cursor position 50 and beginning just short of the region of continuous nasal cavity pressure quiescence as deduced from the pressure pattern 42 and extending two centimeters below that. This region is used to identify the nearest two pressure profiles 44 associated with that region for a one second duration on either side of the cursor position 50. This time duration is intended to comfortably embrace all of the relevant data and could be extended if necessary.

As indicated by process block 54, the user is then instructed to identify the peak pressure of the upper esophagus sphincter (UES) before opening, indicated by cursor position 56. Corresponding cursors may be displayed on the display 37 within the pressure profiles 44 and the pressure pattern 42 (linked by the common data) to assist in this process. The esophageal sphincter is easily recognized in the pressure pattern 42 by a nearly continuous pressure band 58 extending horizontally across the pressure pattern 42 except for a short duration of opening of the esophageal sphincter. In cases where the subject's upper esophageal sphincter has low resting tone and the nearly continuous pressure band is not easily visible, one can use basic knowledge of anatomy and physiology to determine where this region is located within the pressure patterns.

The user is then instructed to identify the peak pressure of the upper esophagus sphincter after closing as indicated by cursor position 60 as indicated by process block 70. It will be noted that these peaks may be on different pressure profiles 44. The cursor positions 56 is then used to automatically determine a pre-opening region 64 encompassing three pressure profiles 44 closest to the cursor position 56 and extending 0.5 seconds on either side of the cursor position 56. The cursor position 60 is used to automatically identify a post-closing region 66 extending downward from the point of maximum pressure at cursor position 60 by a variable number of pressure profiles 44 to the inferior boundary of pre-opening region 64 and extending rightward by one second from cursor position 60. Finally, a relaxation region 68 is automatically defined by the program 40 extending between the cursor positions 56 and 60 and extending as high as the previously highest pressure profile 44 associated with the upper esophageal sphincter to the inferior boundary of pre-opening region 64.

At process block 73, as shown in FIG. 3, the program 40 automatically identifies a mesopharynx region 72 by establishing a test window between velopharynx region 52 and the highest region 64, 68 and 66, with the duration of approximately 2 seconds and a background window with a duration of 2 seconds outside of this test window. The mean and standard deviation of background noise in the background is then determined and the mesopharynx region 72 is defined such as to embrace all pressures higher than the mean background pressure plus at least one standard deviation. At process block 74, the program 40 then extracts a number of parameters for velopharynx region 52 and mesopharynx region 72 including: maximum pressure within the region, maximum rise time in pressure within the region, maximum fall time in pressure within the region, duration of pressure above the baseline, and maximum rise rate of pressure within the region.

For pre-opening region 64 and post-closing region 66, additional parameters may be extracted including maximum pressure and time when it occurs. The time lapse between the maximal pressure in the pre-opening and post-closing pressures is referred to as upper esophageal sphincter activity time. For relaxation region 68, minimum pressure and onset time, sphincter opening time and nadir pressure duration (bolus passage time) are calculated. In this process all of the sensors associated with the upper esophagus sphincter are first combined and then the second order derivative is used to find the onset and offset times of the nadir. Total swallow duration is also calculated as the time between the onset of the velopharynx region 52 and cursor position 60.

For all five regions, two-dimensional pressure integrals are obtained for each pressure profile 44 (the area under the curve of the single sensor 21 above the baseline level) to include the highest recorded pressure and three-dimensional integrals defined as the sum of the two-dimensional pressure integrals for all pressure profiles 44 in the region. These data and typical ranges for normal and abnormal swallowing are provided below in Table I.

TABLE I

Summary Data for the Normal and Abnormal Swallowing.

| Parameter | Normal | Abnormal |
|---|---|---|
| VP duration(s) | 0.70 ± 0.16 | 0.67 ± 0.25 |
| VP rise time(s) | 0.28 ± 0.15 | 0.31 ± 0.19 |

TABLE I-continued

Summary Data for the Normal and Abnormal Swallowing.

| Parameter | Normal | Abnormal |
|---|---|---|
| VP rise rate (mmHg/s) | 712 ± 2578 | 671 ± 1023 |
| VP fall time(s) | 0.42 ± 0.12 | 0.36 ± 0.17 |
| VP maximum pressure (mmHg) | 139 ± 33 | 145 ± 45 |
| VP 2-D integral (mmHg * s) | 52 ± 18 | 64 ± 30 |
| VP 3-D integral (mmHg * s) | 93 ± 33 | 108 ± 50 |
| MP duration(s) | 0.67 ± 0.18 | 0.76 ± 0.36 |
| MP rise time(s) | 0.39 ± 0.17 | 0.38 ± 0.26 |
| MP rise rate (mmHg/s) | 476 ± 682 | 1010 ± 5689 |
| MP fall time(s) | 0.28 ± 0.11 | 0.38 ± 0.24 |
| MP maximum pressure (mmHg) | 134 ± 66 | 122 ± 57 |
| MP 2-D integral (mmHg * s) | 39 ± 20 | 43 ± 26 |
| MP 3-D integral (mmHg * s) | 114 ± 58 | 119 ± 82 |
| UES pre-opening maximum pressure (mmHg) | 108 ± 54 | 95 ± 59 |
| UES pre-opening peak 2-D integral (mmHg * s) | 33 ± 21 | 25 ± 17 |
| UES pre-opening peak 3-D integral (mmHg * s) | 69 ± 35 | 52 ± 33 |
| UES post-closure maximum pressure (mmHg) | 213 ± 84 | 204 ± 129 |
| UES post-closure peak 2-D integral (mmHg * s) | 115 ± 79 | 84 ± 60 |
| UES post-closure peak 3-D integral (mmHg * s) | 318 ± 120 | 251 ± 149 |
| Minimum UES pressure (mmHg) | −1 ± 6 | 0 ± 13 |
| UES activity time(s) | 1.06 ± 0.34 | 0.95 ± 0.36 |
| Nadir duration(s) | 0.54 ± 0.18 | 0.48 ± 0.29 |
| UES 2-D integral (mmHg * s) | 60 ± 55 | 48 ± 39 |
| UES 3-D integral (mmHg * s) | 124 ± 103 | 102 ± 81 |
| Swallow duration(s) | 1.03 ± 0.25 | 0.98 ± 0.38 |

VP = velopharynx; mmHg = millimeters of mercury; s = seconds; MP = mesopharynx; 2-D = two-dimensional; 3-D = three-dimensional; UES = upper esophageal sphincter.

In the above table, upper esophageal sphincter activity time is the time lapse between the pre-opening upper esophageal sphincter pressure peak and the post-closure upper esophageal sphincter pressure peak. The two-dimensional integrals are integrals along single pressure profiles 44 while the three-dimensional integrals are the sums of integrals along multiple pressure profiles 44.

Elements of this process are described in Zhixian Geng, Three-Dimensional Analysis of Pharyngeal High-Resolution Manometry Data, Laryngoscope, 2013, Feb. 16, doi: 10.1002/lary.23987 (E publication) Laryngoscope (2013), PMID 23417441, hereby incorporated in its entirety by reference.

Referring still to FIG. 3, these latter parameters, which are automatically extracted from the regions described above by the program 40 according to well understood techniques, are then applied to a supervised learning machine such as an artificial neural network which maps all or a subset of these parameters to particular diagnostic information. As will be discussed in more detail below, this diagnostic information may simply be identification of abnormal swallowing or, in the case of abnormal swallowing, a diagnosis for the cause of the abnormality, specific aspect of the swallowing process which is abnormal, or clinical parameters useful for making a diagnosis, or identifying a therapeutic target.

In one example, the artificial neural network may be provided by the Neural Network Tool Box of MATLAB which is commercially available from MathWorks of Massachusetts, USA.

Figure 4:
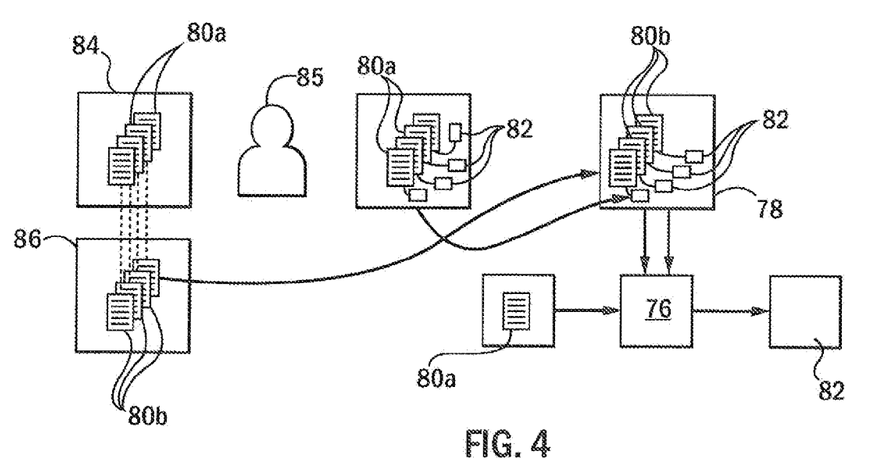
FIG. 4 is a block diagram of the steps of development of a training set and training of the supervised machine learning of FIG. 3.

Referring now to FIG. 4, as is generally understood in the art, supervised machine learning relies on the training of a supervised learning machine 76 using a training set 78 comprised of multiple data sets 80 of the type that need to be analyzed (e.g., the parameters described above associated with a swallow) tagged with the desired outputs 82 (e.g., the diagnoses outputs) to which each given data set 80 should be mapped. After training, an "undiagnosed" data set 80' may be provided to the supervised learning machine 76 to produce diagnostic outputs 82'.

In one embodiment, the necessary training set 78 may be developed by acquiring multiple data sets 80a using x-ray fluoroscopy acquisition 84 and corresponding data sets 80b using manometric acquisition 86 with the manometry system 10 described above. These acquisitions may be performed simultaneously for the same patients and swallows by using the manometry system 10 while the patient is undergoing x-ray fluoroscopy. Each corresponding data set 80a and 80b will be associated with a given swallow by that individual.

In an alternative embodiment, the necessary training set 78 may be developed by acquiring multiple data sets 80a using functional endoscopic evaluation of swallowing (FEES) and corresponding data sets 80b using the manometric acquisition 86 with the manometry system 10 described above. These endoscopic data sets 80b would then be used in lieu of the x-ray fluoroscopy data sets 80b described above for the following steps.

The data sets 80a associated with the x-ray fluoroscopy acquisitions 84 may then be scored by trained individuals 85 to assign each data set 80a to diagnosis outputs 82. In one embodiment, the diagnosis outputs 82 are a subset of the standard parameter set extracted from x-ray fluoroscopy images, for example, being the MBSImP components described in Martin-Harris B, Brodsky M B, Michel Y, et al. MBS measurement tool for swallow impairment—MBSImp: establishing a standard. Dysphagia. 2008; 23:392-405. One subset, including pharyngeal related variables of the MBSImP but excluding oral and esophageal variables, is listed in the following Table II.

TABLE II

Adapted version of the Modified Barium Swallow Impairment Profile.

| Component Number | Description | Score Range |
|---|---|---|
| 6 | Initiation of pharyngeal swallow | 0-4 |
| 8 | Laryngeal elevation | 0-3 |
| 9 | Anterior hyoid excursion | 0-2 |
| 10 | Epiglottic movement | 0-2 |
| 12 | Pharyngeal stripping wave | 0-2 |
| 14 | Pharyngoesophageal segment closing | 0-3 |
| 15 | Tongue base retraction | 0-4 |
| 16 | Pharyngeal residue | 0-4 |

Each data set 80a may also be evaluated according to a Penetration-Aspiration Scale described generally in: Rosenbek J C, Robbins J A, Roecker E B, et al. "A penetration aspiration scale", Dysphagia 1996; 11:93-98 according to the values: 1=no airway invasion, 2-5=penetration, 6-8=aspiration.

The diagnoses values related to the data set 80a are then attached to the corresponding data set 80b to provide the training set used to train the supervised learning machine 76 according to methods well understood in the art.

Figure 5:
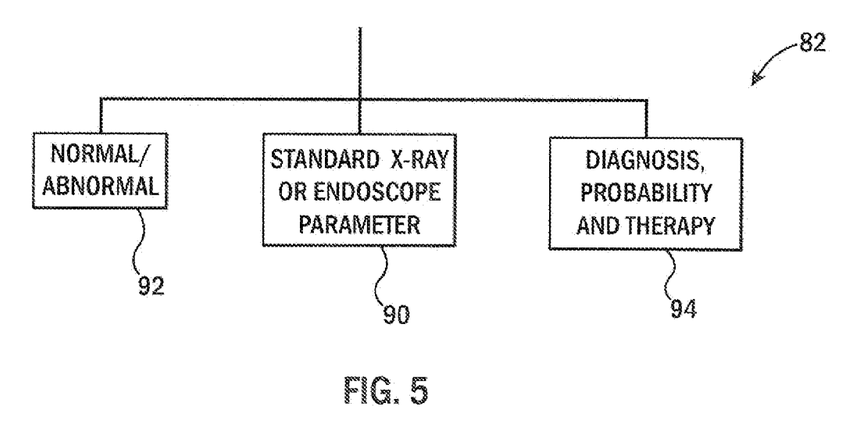
FIG. 5 is a flowchart showing alternative displays of diagnostic information per the flowchart of FIG. 3.

Referring again to FIGS. 3 and 4, after training, manometric data set 80'a may be acquired for a new patient and this data set 80'a applied to the trained supervised learning machine 76 as indicated by process block 88 of FIG. 3. Referring also to FIG. 5, trained supervised learning machine 76 will then produce the output 90, in this case the numeric values of the parameters of Table II normally associated with x-ray fluoroscopy but in this case being acquired solely by manometry or numeric values associated with endoscopic examination.

It will be appreciated that alternatively, or in addition, the diagnostic outputs 82 of the training set may simply be the diagnoses 92 of normal or abnormal as identified, for example, from the Table I whose values were also determined by trained individuals.

Alternatively it is expected that an output 94 providing a more detailed diagnosis indicating the underlying etiology of the swallowing disorder may be provided by scoring data set 80b or data set 80a according to particular etiologies such as cricopharyngeus abnormality, glottic insufficiency, pharyngeal stiffness/fibrosis, neurological, Zenker's diverticulum, head and neck cancer, recurrent hiatal hernia, idiopathic muscular atrophy, Schatzki's ring. For the convenience of the physician, each of these more detailed diagnoses may also be accompanied or linked to appropriate therapies. The probability of accuracy of the diagnosis may also be extracted from the supervised learning machine 76, for example, using the relative weights assigned to each possible diagnosis output 82.

EXAMPLE 1

Procedure: 335 swallows from 30 subjects were analyzed using both manometry and x-ray videofluoroscopy. Videofluoroscopy was performed in the lateral plane at 30 frames per second (Axiom Sireskop SD, Siemens, Munich, Germany or OEC 9900, General Electric, Fairfield, Conn.). Video was digitized and recorded onto a DVD1RW for offline analysis (DVO-1000MD, Sony, Park Ridge, N.J.). A solid-state high-resolution manometer with 36 sensors and outer diameter of 4 mm was used for manometry (ManoScan360 High Resolution Manometry System, Sierra Scientific Instruments, Los Angeles, Calif.).

The catheter was covered with a protective sheath during testing (ManoShield, Sierra Scientific Instruments) and calibrated before each use according to manufacturer specifications. Data were collected at a sampling rate of 50 Hz (ManoScan Data Acquisition, Sierra Scientific Instruments).

Thirty subjects participated in this study with the approval of the University of Wisconsin-Madison Institutional Review Board. Subjects were comprised of 19 males and 11 females, with a mean age of 68.0±11.8 years (range, 40-87). A small amount of topical 2% viscous lidocaine hydrochloride was applied to the nasal passages and catheter to provide local anesthesia and ease catheter insertion. Participants were seated upright within the video fluoroscopic unit for the entire procedure. Boundaries for the video fluoroscopic frame included the incisors anteriorly, cervical vertebrae posteriorly, nasal border of the soft palate superiorly, and cervical esophagus inferiorly. Correct catheter placement was verified on videofluoroscopy. Once the catheter was in place, participants rested for 5 to 10 minutes to adjust to the catheter before performing experimental swallows. Participants swallowed between 2 and 30 total boluses of 5 ml, 10 ml, and self-selected amounts of thin-liquid, nectar-thick liquid, honey-thick liquid, or pudding barium sulfate (Varibar, E-Z-EM, Lake Success, N.Y.) based on their ability to safely tolerate those consistencies, as judged by a certified speech-language pathologist. All swallows were performed with the head in a neutral position.

Premeasured boluses were given via syringe and self-selected sips were taken via straw. A straw was used for self-selected sip trials, as it was difficult to drink from a cup without a straw while the catheter was in place. Participants were instructed to hold the bolus in the mouth until cued to swallow by the experimenter.

Video fluoroscopic studies were scored according to the MBSImP parameters described above. Known swallows (both classification and data are provided) are presented during a training stage and unknown swallows (only data are provided) are presented during a testing stage. Training and testing data are kept separate to increase generalizability of the classification algorithm. Data were randomly partitioned into a training set (60%), a testing set (20%), and a validation set (20%). A Multi-Layer Perceptron ANN was created using sigmoidal activation functions in 1 hidden layer, with the number of hidden nodes varying from 10 to half of the total number of samples included to achieve optimal performance. Twenty replicates were performed at each number of hidden nodes to determine classification accuracy and reliability.

Results: MBSImP parameters were identified correctly as normal or disordered at an average rate of approximately 91% (area under the ROC curve ranged from 0.902 to 0.981). Classifications incorporating two MBSImP parameters resulted in classification accuracies over 93% (area under the ROC curve ranged from 0.963 to 0.989).

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained

What we claim is:

1. A system for diagnosing swallowing disorders of a patient comprising:
   a manometer adapted to be inserted along the upper aerodigestive tract in the vicinity of the patient's pharynx and esophagus to provide a series of pressure measurements at different points along the patient's pharynx;
   a computer receiving the series of pressure measurements at different points and executing a stored program to:
   (a) link the pressure measurements during a swallowing to different multiple predetermined locations along the pharynx;
   (b) analyze pressure as a function of time in the predetermined locations to generate a set of pressure based predetermined parameters;
   (c) process the pressure based predetermined parameters to derive image-describing diagnostic parameters and values that conform to a modified barium swallow impairment profile (MBSImP); and
   (d) output the image-describing diagnostic parameters and values to a user.

2. The system of claim 1 wherein the linking of pressures to predetermined locations identifies the predetermined locations with respect to pressure pattern having dimensions of distance along the pharynx and time.

3. The system of claim 2 wherein the identification of the predetermined locations receives input from a user viewing time pressure pattern identifying at least one point associated with a predetermined location.

4. The system of claim 3 wherein the stored program combines at least one point received from the user with other data from the pressure pattern to identify the predetermined locations.

5. The system of claim 1 wherein the manometer provides for pressure measurements no greater than 1 cm separation along the pharynx.

6. The system of claim 5 wherein the predetermined locations include the patient's velopharynx, and esophageal sphincter.

7. The system of claim 6 wherein the computer further executes a stored program to determine a time of opening of the upper esophageal sphincter.

8. The system of claim 6 wherein the pressure based predetermined parameters for the predetermined locations are selected from the group consisting of: maximum pressures, rise time, rise rate, fall-time, duration of pressure above a baseline, duration between opening and closure peak pressures, and nadir pressure duration.

9. The system of claim 8 wherein the maximum pressures include peak pressure before opening of the esophageal sphincter and a maximum pressure after opening of the esophageal sphincter.

10. The system of claim 6 wherein the predetermined locations include the patient's mesopharynx.

11. The system of claim I wherein the image-describing diagnostic parameters and values provide an indication of normal or abnormal swallowing function.

12. The system of claim 11 wherein the diagnosis provides an indication of a cause of the swallowing disorder selected from the group consisting of cricopharyngeus abnormality, glottic insufficiency, pharyngeal stiffness/fibrosis, neurological disorder, Zenker's diverticulum, head and neck cancer, recurrent hiatal hernia, idiopathic muscular atrophy, Schatzki's ring, generalized weakness, and discoordintation.

13. The system of claim 12 wherein the image-describing diagnostic parameters and values includes a confidence value indicating a confidence in the diagnosis.

14. The system of claim 12 wherein, the computer further executes a stored program to display a recommended therapy.

15. The system of claim 1 wherein the processing employs supervised machine learning based on a training set of clinically acquired swallow measurements linked to a diagnostic value.

16. The system of claim 1 wherein the image-describing diagnostic parameters describe motion of the patient's pharynx and esophagus.

17. The system of claim 16 wherein the image-describing diagnostic parameters include at least one of: Laryngeal elevation, Anterior hyoid excursion, and Epiglottic movement.

18. A system for diagnosing swallowing disorders of a patient comprising:
   a manometer adapted to be inserted along the upper aerodigestive tract in the vicinity of the patient's pharynx and esophagus to provide a series of pressure measurements at different points along the patient's pharynx;
   a computer receiving the series of pressure measurements at different points and executing a stored program to:
   (a) link the pressure measurements during a swallowing to different multiple predetermined locations along the pharynx;
   (b) analyze pressure as a function of time in the predetermined locations to generate a set of predetermined parameters;
   (c) map the parameters to diagnostic parameters and values provided by videofluoroscopic assessment indicating swallowing function; and
   (d) output the diagnostic parameters and values to a user wherein the diagnostic parameters and values conform to a modified barium swallow impairment profile (MBSImP).

19. The system of claim 18 wherein, the diagnostic parameters and values are selected from the group consisting of initiation of pharyngeal swallow, laryungeal elevation, anterior hyoid excursion, epiglottic movement, pharyngeal stripping wave, pharyngoesophageal segment closing, tongue base retraction, and pharyngeal residue.

20. A system for diagnosing swallowing disorders of a patient comprising:
   a manometer adapted to be inserted along the upper aerodigestive tract in the vicinity of the patient's pharynx and esophagus to provide a series of pressure measurements at different points along the patient's pharynx;
   a computer receiving the series of pressure measurements at different points and executing a stored program to:
   (a) link the pressure measurements during a swallowing to different multiple predetermined locations along the pharynx;
   (b) analyze pressure as a function of time in the predetermined locations to generate a set of predetermined parameters;

(c) map the parameters to diagnostic parameters and values provided by videofluoroscopic assessment indicating swallowing function; and (d) output the diagnostic parameters and values to a user;

wherein the mapping employs supervised machine learning based on a training set of clinically acquired swallow measurements linked to a diagnostic value; and wherein the linking to a diagnostic value employs contemporary measurements with the manometer and modified barium swallow impairment profile (MB-SImP).

21. A method for diagnosing dysphagia employing a dysphagia assessment system comprising the steps of:

providing a dysphagia assessment system comprising a manometer adapted to be inserted along a patient's pharynx to provide a series of pressure measurements at different points along the pharynx;

a computer receiving the series of pressure measurements at different points and executing a stored program to;

link pharyngeal pressures during a swallowing to different multiple predetermined locations along the pharynx;

analyze pressure as a function of time in the predetermined locations to generate a set of predetermined pressure parameters;

process the pressure parameters to derive image-describing diagnostic parameters and values that conform to a modified barium swallow impairment profile (MB-SImP); and output the image-describing diagnostic parameters and values to a user;

wherein the method comprises the steps of:

(a) obtaining clinical measures of swallowing of multiple individuals using the manometer to produce a training set of pharyngeal pressures during a swallowing to multiple predetermined locations along the pharynx for the multiple individuals;

(b) categorizing the training set according to categories of diagnostic values.

22. The method of claim 21 wherein the clinical measures simultaneously provide high definition manometric data and at least one of videofluoroscopy and functional endoscopic evaluation of swallowing (FEES).

\* \* \* \* \*